US010188806B2

(12) United States Patent
Schabbach et al.

(10) Patent No.: US 10,188,806 B2
(45) Date of Patent: Jan. 29, 2019

(54) DRIVE MECHANISM FOR A NEEDLE INSERTION ARRANGEMENT

(71) Applicant: Sanofi-Aventis Deutschland GMBH, Frankfurt am Main (DE)

(72) Inventors: Michael Schabbach, Frankfurt am Main (DE); Meinolf Werner, Worms (DE); Olaf Zeckai, Weinheim (DE); Philippe Nzike, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 332 days.

(21) Appl. No.: 14/916,662

(22) PCT Filed: Sep. 2, 2014

(86) PCT No.: PCT/EP2014/068594
§ 371 (c)(1),
(2) Date: Mar. 4, 2016

(87) PCT Pub. No.: WO2015/032740
PCT Pub. Date: Mar. 12, 2015

(65) Prior Publication Data
US 2016/0199590 A1     Jul. 14, 2016

(30) Foreign Application Priority Data
Sep. 5, 2013   (EP) ..................................... 13183149

(51) Int. Cl.
*A61M 5/32*     (2006.01)
*A61M 5/34*     (2006.01)
*A61M 5/158*     (2006.01)

(52) U.S. Cl.
CPC .......... *A61M 5/3287* (2013.01); *A61M 5/158* (2013.01); *A61M 5/34* (2013.01); *A61M 2005/1585* (2013.01)

(58) Field of Classification Search
CPC ...... A61M 5/3287; A61M 5/158; A61M 5/34; A61M 2005/1585
See application file for complete search history.

(56) References Cited

U.S. PATENT DOCUMENTS

2005/0245956 A1* 11/2005 Steinemann .......... A61M 5/158
                                                                                  606/185
2008/0269639 A1* 10/2008 Korner ............. A61B 5/150022
                                                                                  600/583

(Continued)

FOREIGN PATENT DOCUMENTS

| EP | 1764037 | 3/2007 |
| EP | 1970091 | 9/2008 |
| EP | 2452709 | 5/2012 |

OTHER PUBLICATIONS

International Search Report and Written Opinion in International Application No. PCT/EP2014/068594, mailed Nov. 7, 2014, 11 pages.

(Continued)

*Primary Examiner* — Nathan R Price
*Assistant Examiner* — Dung Ulsh
(74) *Attorney, Agent, or Firm* — Fish & Richardson P.C.

(57) ABSTRACT

The invention relates to a drive mechanism (9) for a needle insertion arrangement (1), the drive mechanism (9) being arranged as a bistable mechanism with at least one pivoted link (10, 11) having two stable end positions (LEP, UEP) and an instable transitional central position (CP), the drive mechanism (9) further comprising a spring (12) biasing the link (10, 11) out of the transitional central position (CP), wherein at least one trigger unit (17, 21) is arranged for (Continued)

moving the link (10, 11) out of at least one of the stable end positions (LEP, UEP) towards and beyond the transitional central position (CP) against the bias of the spring (12).

18 Claims, 14 Drawing Sheets

(56) References Cited

U.S. PATENT DOCUMENTS

| | | | |
|---|---|---|---|
| 2011/0152717 A1 | 6/2011 | Kim et al. | |
| 2013/0110049 A1* | 5/2013 | Cronenberg | A61M 5/14248 604/180 |
| 2016/0193405 A1* | 7/2016 | Schabbach | A61M 5/3287 604/156 |
| 2016/0199590 A1* | 7/2016 | Schabbach | A61M 5/3287 604/240 |
| 2016/0213837 A1* | 7/2016 | Schabbach | A61M 5/158 |
| 2016/0213838 A1* | 7/2016 | Schabbach | A61M 5/3287 |
| 2016/0213840 A1* | 7/2016 | Schabbach | A61M 5/3287 |
| 2016/0317754 A1* | 11/2016 | Schader | A61M 5/326 |
| 2016/0354553 A1* | 12/2016 | Anderson | A61M 5/3298 |

OTHER PUBLICATIONS

International Preliminary Report on Patentability in Application No. PCT/EP2014/068594, dated Mar. 8, 2016, 9 pages.
Rote Liste, "50. Hypophyses-, Hypothalamushormone, andere regulatorische Peptide u. ihre Hemmstoffe," Chapter 50, ed. 2008, 20 pages.

\* cited by examiner

DRIVE MECHANISM FOR A NEEDLE INSERTION ARRANGEMENT

CROSS-REFERENCE TO RELATED APPLICATIONS

This application is a U.S. national stage application under 35 USC § 371 of International Application No. PCT/EP2014/068594, filed on Sep. 2, 2014, which claims priority to European Patent Application No. 13183149.7, filed on Sep. 5, 2013, the entire contents of which are incorporated herein by reference.

TECHNICAL FIELD

The invention relates to a drive mechanism for a needle insertion arrangement.

BACKGROUND OF THE INVENTION

Administering an injection is a process which presents a number of risks and challenges for users and healthcare professionals, both mental and physical. During manual insertion of an injection needle into an injection site, e.g. the skin of a patient, it may be difficult to avoid tilting and bending of the needle and the insertion may be slow thus causing pain.

There remains a need for an improved drive mechanism for a needle insertion arrangement.

EP 1 764 037 A1 discloses a device for collecting body fluids, the device having a pricking unit prickable in a body part, and a drive that is provided for forward and backward running pricking movement of the pricking unit. The drive has actuator wires on the basis of a shape memory alloy (SMA) for control of the pricking movement by a change of wire length. The wires serve as brake unit for braking of the backward movement of the pricking unit. The actuator wire forms a feed unit for forward movement of the pricking unit through heat-activated contraction. The drive has an actuator formed by an electro-active polymer.

SUMMARY OF THE INVENTION

Aspects of the present invention can include providing an improved drive mechanism for a needle insertion arrangement.

The aspects can be implemented by a drive mechanism for a needle insertion arrangement according to claim 1.

Exemplary embodiments of the invention are given in the dependent claims.

According to the invention a drive mechanism for a needle insertion arrangement, the drive mechanism being arranged as a bistable mechanism with at least one pivoted link having two stable end positions and an instable transitional central position, the drive mechanism further comprising a spring biasing the link out of the transitional central position, wherein at least one trigger unit is arranged for moving the link out of at least one of the stable end positions towards and beyond the transitional central position against the bias of the spring.

According to the invention the drive mechanism further comprises a forked needle retainer adapted to retain an injection needle, the needle retainer arranged to be moved between a retracted position and an extended position, wherein one end of the link is adapted to abut an upper prong and a lower prong on the forked needle retainer.

In an exemplary embodiment the link comprises a cam for engaging the upper prong and the lower prong.

In an exemplary embodiment the upper prong is spaced from the lower prong for allowing a pre-determined free travel of the link between disengaging one of the prongs and engaging the other one of the prongs.

In an exemplary embodiment the drive mechanism further comprises a first link and a second link interconnected by a pivot joint such that pivoting movement of one of the links causes pivoting movement of the other one of the links.

In an exemplary embodiment the second link comprises a first part and a second part telescoped with each other such that the length of the second link is changed when the second link is being pivoted.

In an exemplary embodiment the first link is connected to an anchor point by a first pivot joint, wherein one end of the second link is connected to another anchor point by a second pivot joint having a fixed position relative the first pivot joint.

In an exemplary embodiment the first part and the second part of the second link are biased apart by the spring.

In an exemplary embodiment the trigger unit is arranged as a button connected to one of the links.

In an exemplary embodiment the drive mechanism further comprises a button link pivoted about a fourth pivot joint in the button with one end and comprising a button cam for engaging a guide track in the first link, wherein the first pivot joint is arranged between two ends of the guide track.

In an exemplary embodiment the guide track comprises a long slot allowing movement of the button cam from one end of the guide track to the other after the first link having been moved to one of the stable end positions and after release of the button such that another operation of the button switches the first link into the respective other one of the stable end positions.

In an exemplary embodiment the guide track comprises a first bulge at one end of the guide track and a second bulge at another end of the guide track.

In an exemplary embodiment the trigger unit is arranged as a motor-driven wheel comprising a first protrusion adapted to engage the first link when the wheel is rotated in a first rotational direction and comprising a second protrusion adapted to engage the first link when the wheel is rotated in an opposite second rotational direction.

In an exemplary embodiment the first protrusion and the second protrusion are angularly spaced from each other allowing for a pre-determined free rotation of the first link relative the wheel.

The drive mechanism may be applied in an insertion arrangement for moving an injection needle between a retracted position and an extended position, comprising a disposable unit, comprising a needle base, to which the needle is fixed, and the drive mechanism, wherein the needle retainer is adapted to retain the needle base.

The insertion arrangement has only limited space requirements thus allowing for low profile injection devices with a high wearing comfort. The insertion arrangement achieves high speed needle movements and exact needle guidance thus reducing pain for the patients when inserting and retracting the needle and increasing consumer acceptance and satisfaction. The insertion arrangement may be embodied with manual or motor powered operation. The low part count of the insertion arrangement allows for an increased mechanical robustness and low manufacturing costs. The insertion arrangement is a fault-tolerant system. In the manually operated embodiment a single button is used for triggering both needle insertion and needle retraction.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus, are not limitive of the present invention, and wherein.

Corresponding parts are marked with the same reference symbols in all figures.

DETAILED DESCRIPTION

Figure 1:
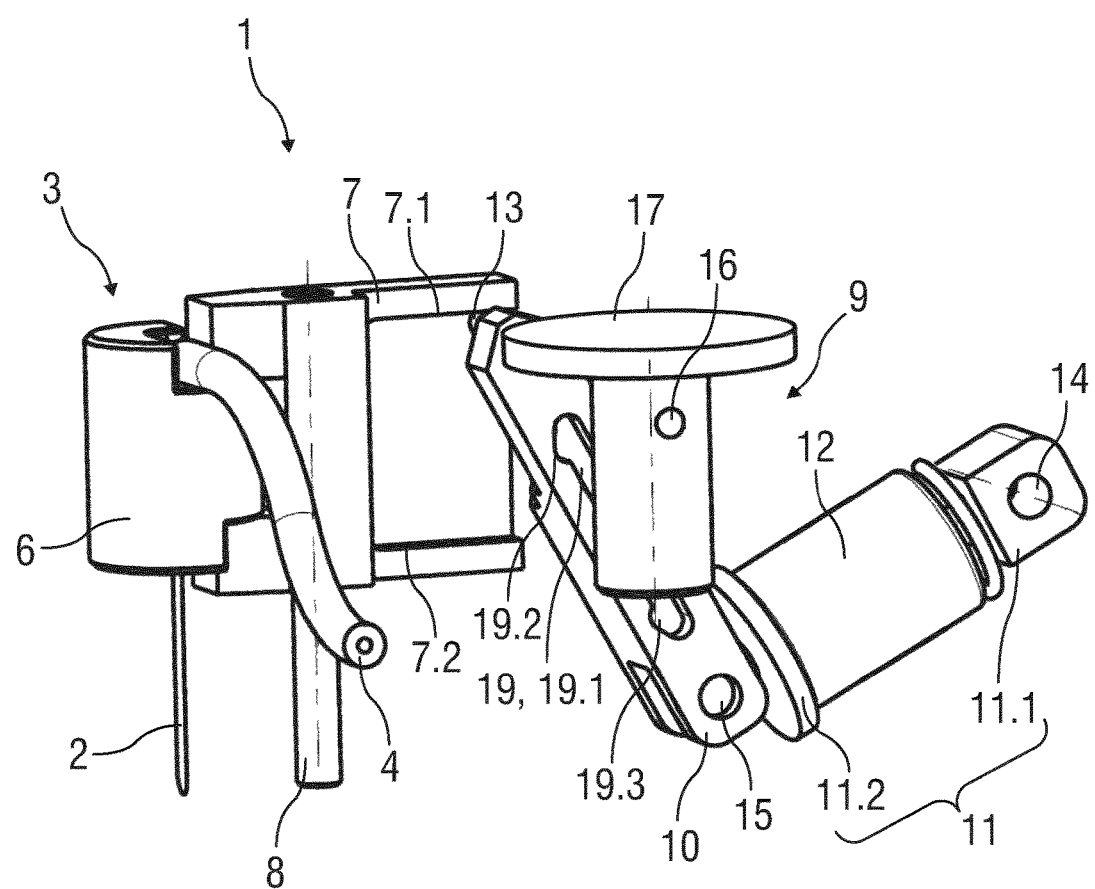
FIG. 1 is a schematic perspective view of an exemplary first embodiment of an insertion arrangement for automatically or semi-automatically inserting an injection needle into an injection site.
Figure 2:
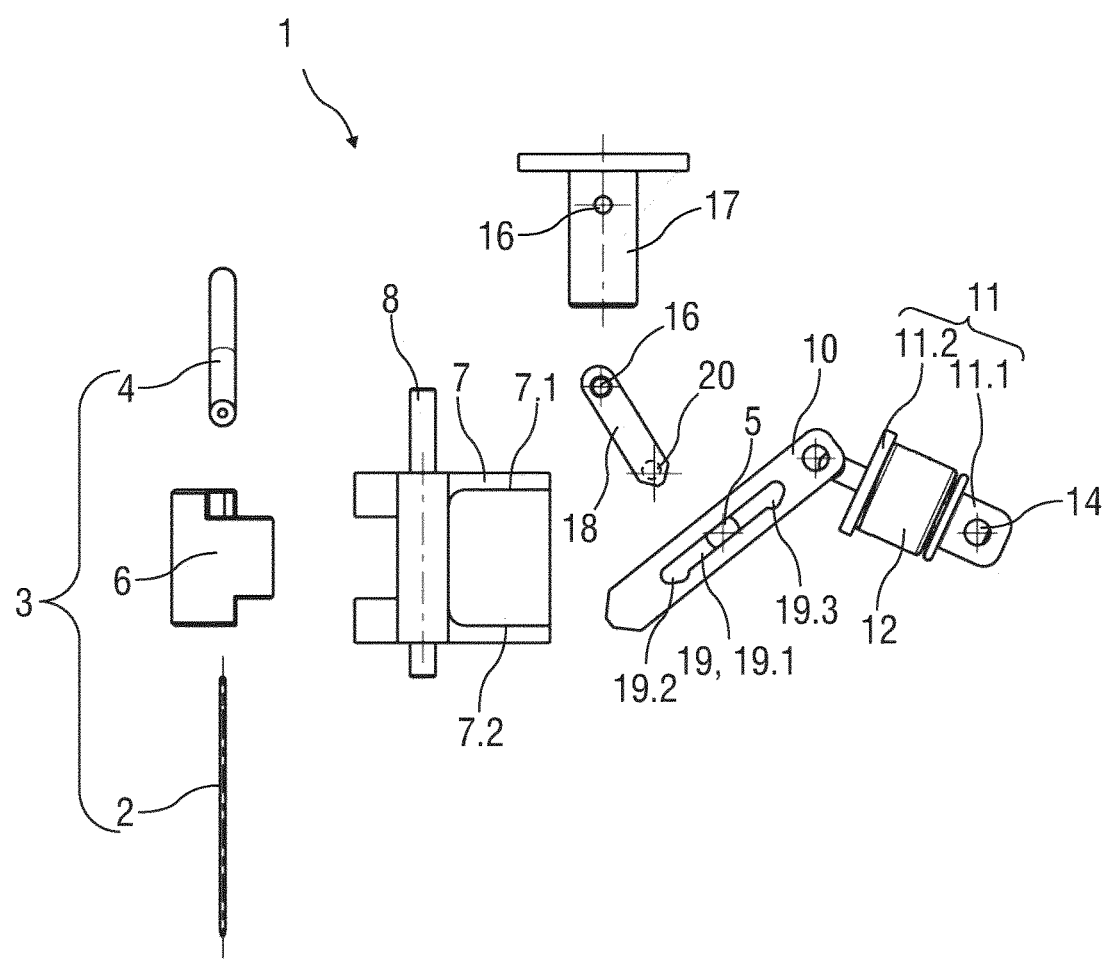
FIG. 2 is a schematic exploded view of the insertion arrangement.

FIG. 1 is a schematic perspective view of an exemplary first embodiment of an insertion arrangement 1 for automatically or semi-automatically inserting an injection needle 2 into an injection site. FIG. 2 is a related exploded view. The injection may be performed manually or by a motor. The arrangement 1 may be applied in medicament pumps, e.g. insulin pumps which may be permanently worn on the body.

The injection needle 2 is part of a disposable unit 3, further comprising a tube 4 for establishing a fluid communication of the needle 2 with a drug container (not illustrated) and comprising a needle base 6, to which the injection needle 2 may be fixed for mechanically connecting the needle 2 to a drive mechanism 9 of an injection unit (not illustrated). The needle base 6 is inserted in a forked needle retainer 7 which is arranged to be moved up and down in a linear guide 8. This linear movement corresponds to insertion of the needle 2 into the injection site, e.g. subcutaneous body tissue and removal from the injection site, respectively.

A drive mechanism 9 for the needle 2 is arranged as a bi-stable mechanism with a first link 10 connected to an anchor point in a case (not illustrated) by a first pivot joint 5 which may be arranged in the middle of the first link 10. One end of the first link 10 is adapted to abut an upper prong 7.1 or a lower prong 7.2 on the forked needle retainer 7 by a cam 13 on the first link 10. The second link 11 comprises a first part 11.1 and a second part 11.2 telescoped with each other. One end of the second link is connected to another anchor point in the case (not illustrated) by a second pivot joint 14 such that the first and second pivot joint 5, 14 cannot move relative each other. The other ends of both the first link 10 and the second link 11 are interconnected by a third pivot joint 15 such that pivoting movement of one of the links 10, 11 causes pivoting movement of the other link 11, 10 thereby also changing the length of the telescopable second link 11. The length of the second link 11 is shortest if the third pivot joint 15 is situated on an imaginary connecting line between the cam 13 and the second pivot joint 14 in a central position. As the third pivot joint 15 is moved above or below the connecting line between the cam 13 and the second pivot joint 14 the length of the second link 11 increases. The first part 11.1 and second part 11.2 of the second link 11 are biased apart by the spring 12 such that the spring 12 is compressed by shortening the second link 11. The force of the spring 12 is therefore highest in the central position of the third pivot joint 15.

The spring force thus forces the third pivot joint 15 out of the central position towards one of two end positions which may be defined by a stop (not illustrated) limiting the maximum length of the second link 11. In these end positions the drive mechanism 9 is stable due to the remaining force of the spring 12 while the central position is transitional.

A button 17 is arranged for switching the drive mechanism 9 between the two stable end positions. A button link 18 is pivoted by a fourth pivot joint 16 in the button 17 with one end and comprises a button cam 20 for engaging a guide track 19 in the first link 10. The guide track 19 comprises a long slot 19.1 with a lateral first bulge 19.2 near the cam 13 and a lateral second bulge 19.3 near the third pivot joint 15 at the ends of the long slot 19.1 for ensuring that after having switched the drive mechanism 9 to one of the stable end positions the button link 18 is engaged to that end of the guide track 19 which must be acted upon for switching the drive mechanism 9 into the respective other stable end position.

Figure 3:
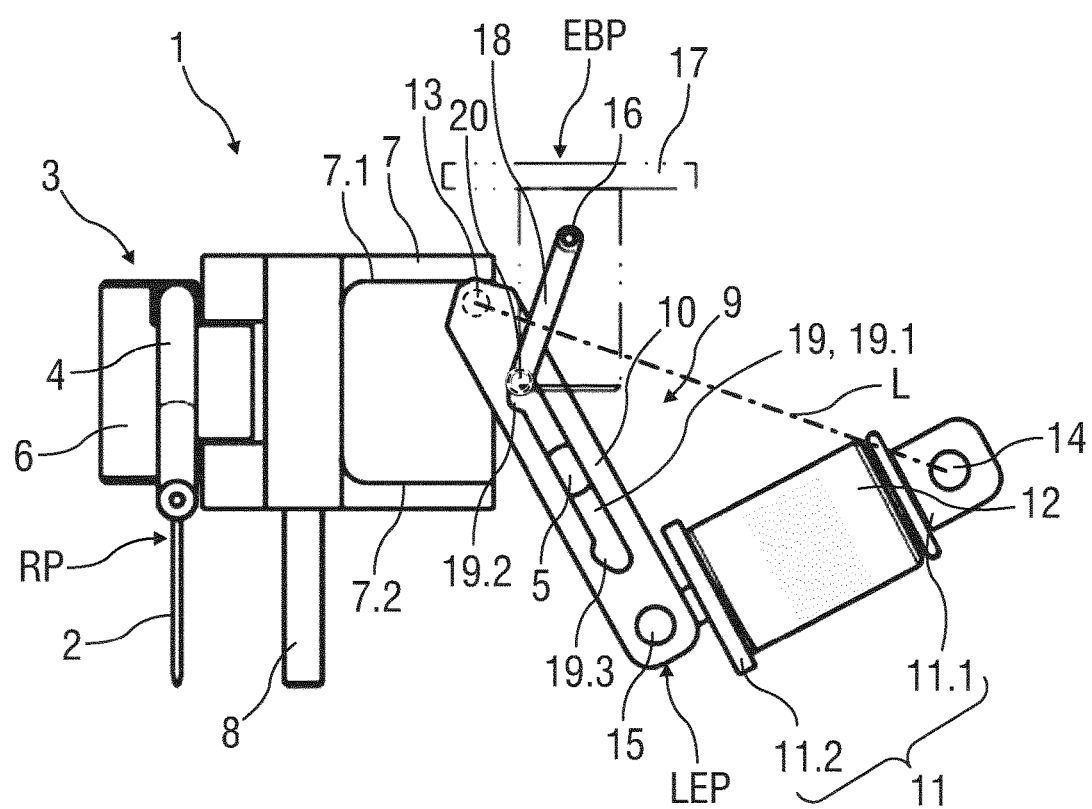
FIG. 3 is a schematic side view of the insertion arrangement in an initial position with a bistable drive mechanism in a stable lower end position and the needle in a retracted position.

A sequence of operation of the insertion arrangement 1 is as follows:

FIG. 3 is a schematic side view of the insertion arrangement 1 in an initial position. The disposable unit 3 with the needle base 6, the needle 2 and the tube 4 has been inserted in the forked needle retainer 7. The third pivot joint 15 is held in a stable lower end position LEP below an imaginary connecting line L between the cam 13 and the second pivot joint 14 by the spring 12. The cam 13 thus engages the upper prong 7.1 on the forked needle retainer 7 keeping it in a retracted position RP. The button cam 20 on the button link 18 is engaged in the first bulge 19.2 of the guide track 19 keeping the button 17 in an extended button position EBP.

Figure 4:
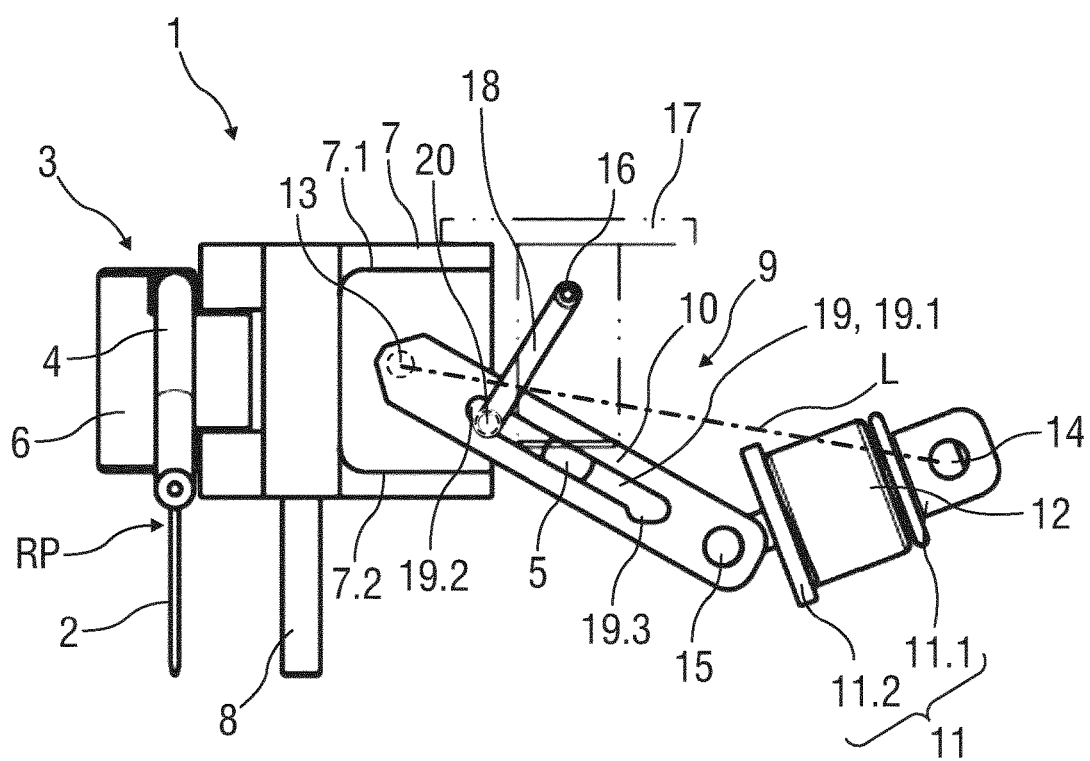
FIG. 4 is a schematic side view of the insertion arrangement during operation of a button.

FIG. 4 is a schematic side view of the insertion arrangement 1 during operation of the button 17. Due to the depression of the button 17 the cam 13 is removed from the upper prong 7.1 on the forked needle retainer 7 towards the lower prong 7.2. The first link 10 is rotated about the first pivot joint 5 thereby telescoping the first part 11.1 and second part 11.2 and further compressing the spring 12. Due to the distance between the upper prong 7.1 and the lower prong 7.2 the cam 13 is disengaged from the forked needle retainer 7 such that the forked needle retainer 7, the needle base 6 and the needle 2 remain in the retracted position RP. A spring or detent (not illustrated) may be arranged for securing the forked needle retainer 7 in the retracted position RP.

Figure 5:
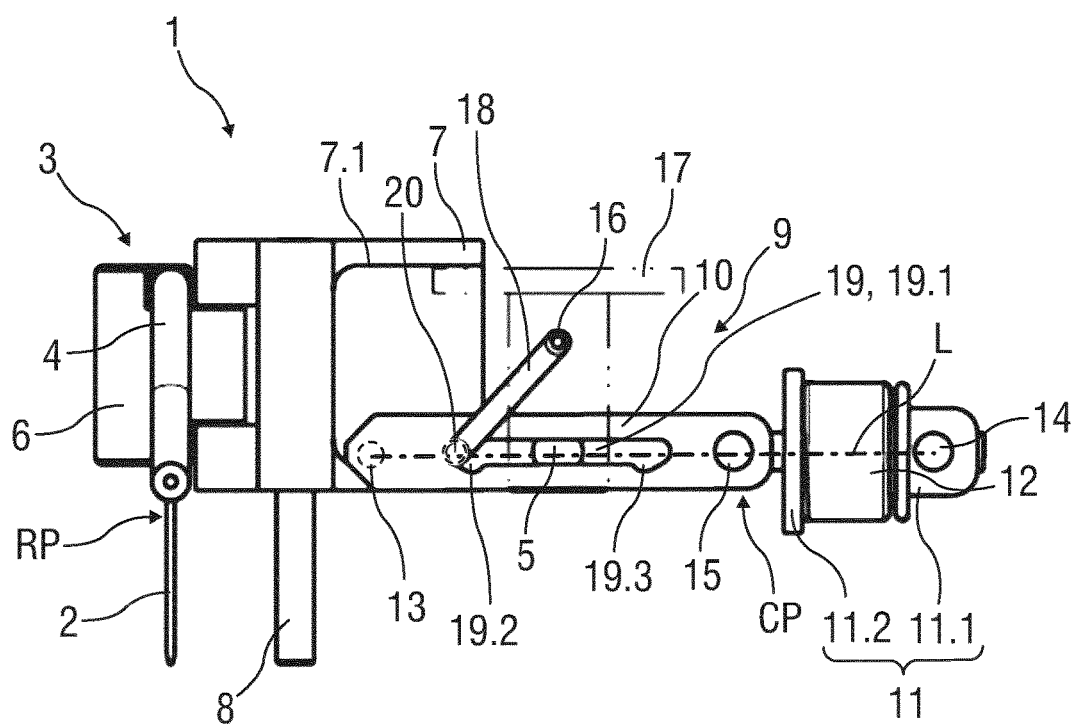
FIG. 5 is a schematic side view of the insertion arrangement with the drive mechanism in a transitional central position.

FIG. 5 is a schematic side view of the insertion arrangement 1 with the third pivot joint 15 in the central position CP. The first link 10, second link 11 and third pivot joint 15 are aligned on the imaginary connecting line L. The spring 12 is therefore fully compressed and the first part 11.1 and second part 11.2 fully telescoped. The cam 13 on the first link 10 is contacting the lower prong 7.2 but not yet exerting any force to it. The forked needle retainer 7, the needle base 6 and the needle 2 therefore remain in the retracted position RP.

Figure 6:
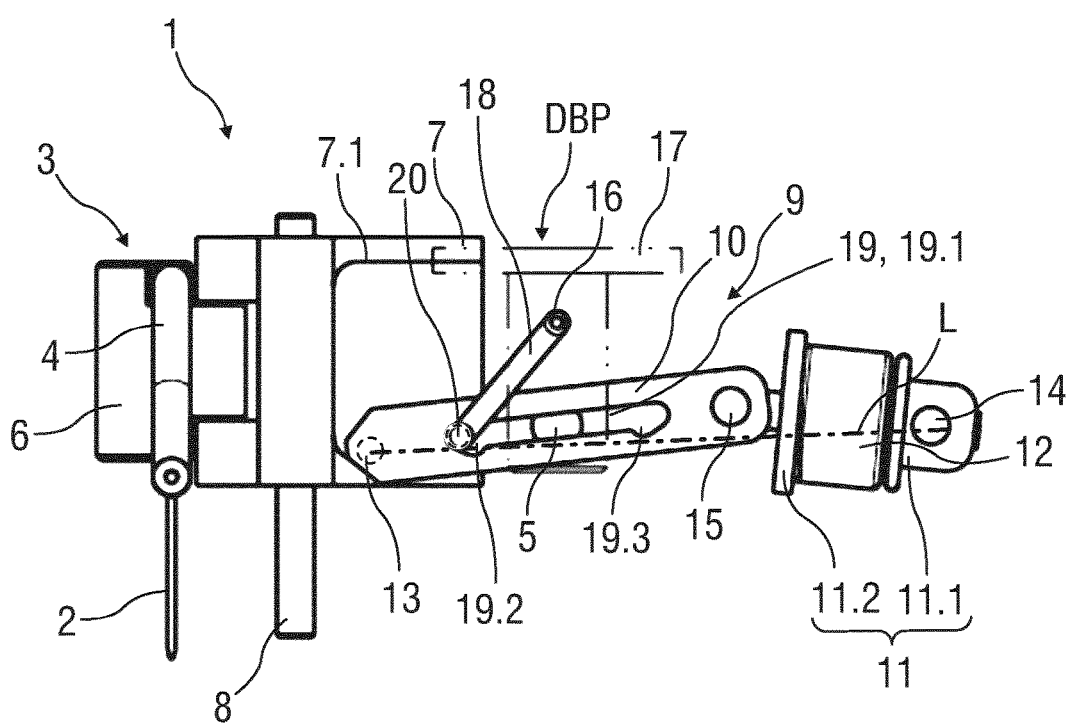
FIG. 6 is a schematic side view of the insertion arrangement with the button further depressed into a depressed button position.

FIG. 6 is a schematic side view of the insertion arrangement 1 with the button 17 further depressed into a depressed button position DBP. Due to the further depression of the button 17 the third pivot joint 15 is moved out of its central position CP below the imaginary connecting line Lines This allows the spring 12 to suddenly relax, telescoping the first part 11.1 and second part 11.2 apart and rotating the first link 10 further such that the cam 13 pushes on the lower prong 7.2 of the forked needle retainer 7 thereby moving the forked needle retainer 7, the needle base 6 and the needle 2 into an extended position EP in order to rapidly inserting the needle 2 into an injection site.

Figure 7:
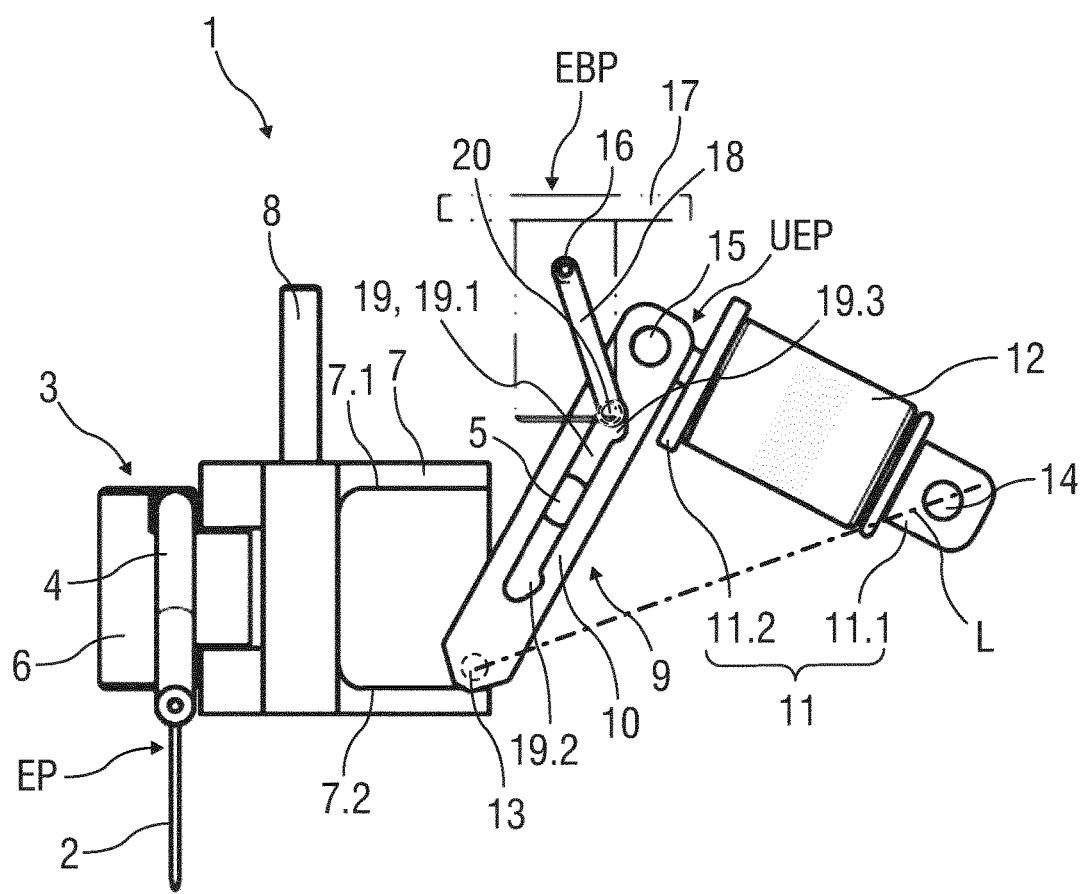
FIG. 7 is a schematic side view of the insertion arrangement with the drive mechanism in a stable upper end position.

FIG. 7 is a schematic side view of the insertion arrangement 1 with the drive mechanism 9 having reached its stable upper end position UEP due to the force of the spring 12. The forked needle retainer 7, needle base 6 and needle 2 have been moved to the extended position EP.

The needle 2 has therefore reached its maximum insertion depth. The user has released the button 17 allowing the button 17 to return to its extended button position EBP. This may be achieved by a further spring (not illustrated). The button link 18 moves with the button 17 pulling the button cam 20 from the first bulge 19.2 along the long slot 19.1 to the second bulge 19.3. The button link 18 is therefore in a position in which depression of the button 17 would cause the drive mechanism 9 to switch to the stable lower end position LEP such that the cam 13 would contact the upper prong 7.1 and retract the forked needle retainer 7, the needle base 6 and the needle 2 into the retracted position RP as in FIG. 3. This switching is achieved in an analogous manner as from the stable lower end position LEP to the stable upper end position UEP. The speed, e.g. slow, middle, fast, of the movement of the forked needle retainer 7 between the retracted position RP and the extended position EP and vice versa can be influenced by selecting a spring 12 with an appropriate force.

Figure 8:
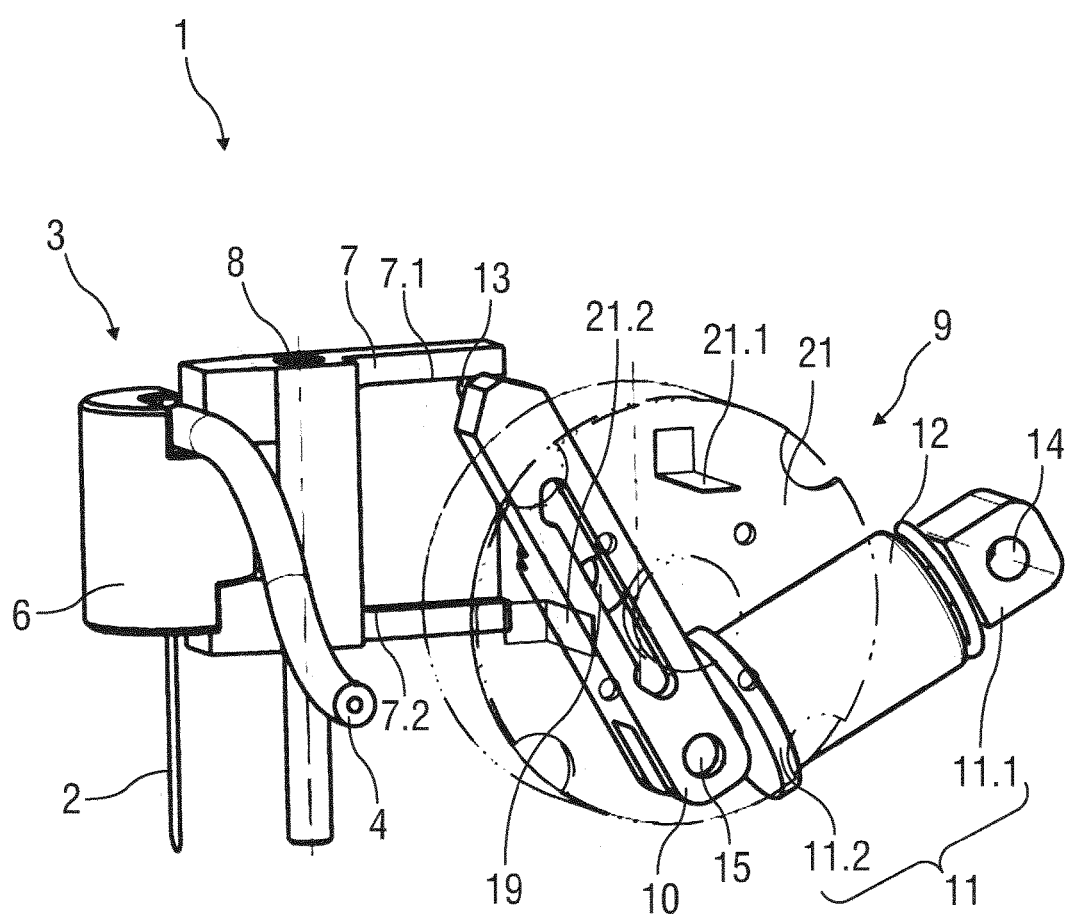
FIG. 8 is a schematic perspective view of a second exemplary embodiment of an insertion arrangement for automatically or semi-automatically inserting an injection needle into an injection site.
Figure 9:
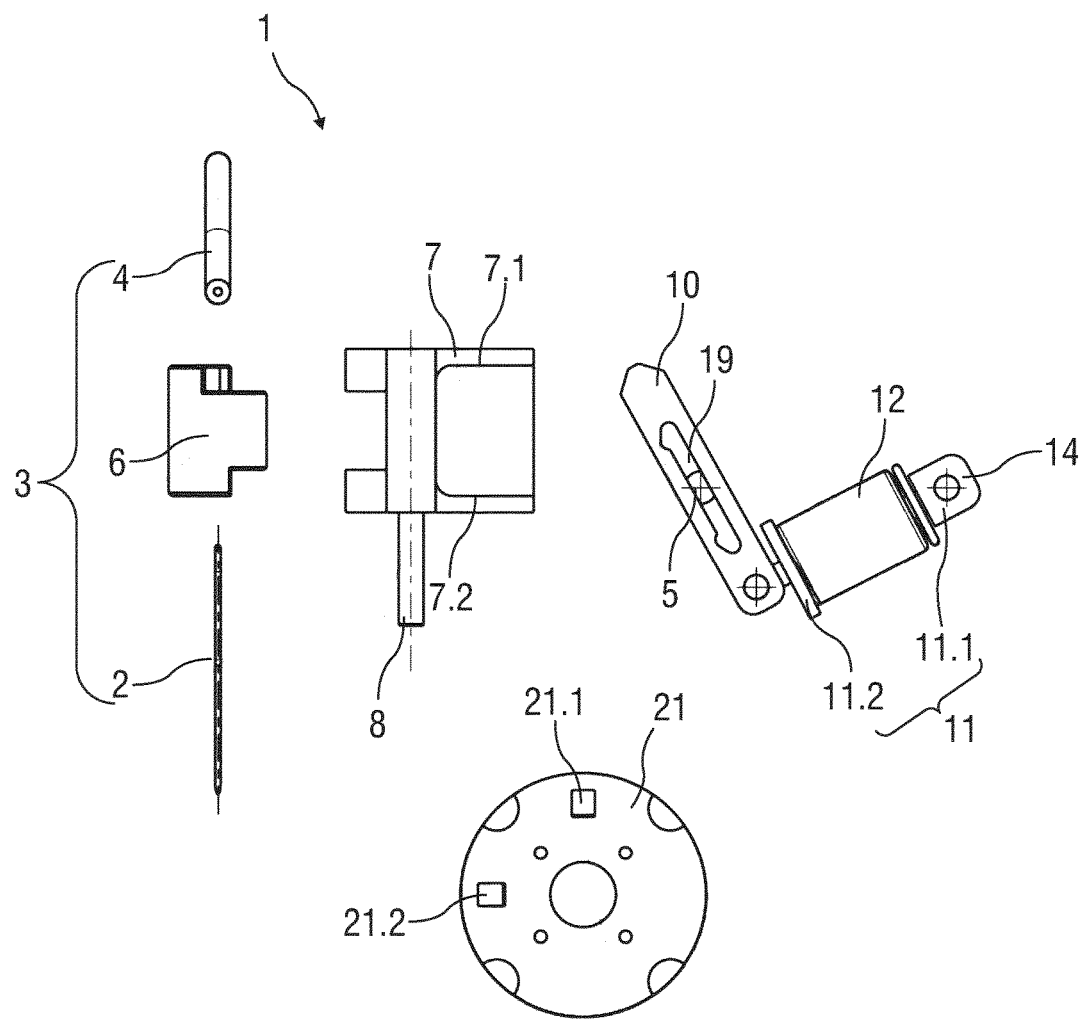
FIG. 9 is a schematic exploded view of the second embodiment of the insertion arrangement.

FIG. 8 is a schematic perspective view of another exemplary embodiment of an insertion arrangement 1 for automatically or semi-automatically inserting an injection needle 2 into an injection site. FIG. 9 is a related exploded view.

The injection needle 2 is part of a disposable unit 3, further comprising a tube 4 for establishing a fluid communication of the needle 2 with a drug container (not illustrated) and comprising a needle base 6, to which the injection needle 2 may be fixed for mechanically connecting the needle 2 to an injection unit (not illustrated). The needle base 6 is inserted in a forked needle retainer 7 which is arranged to be moved up and down in a linear guide 8. This linear movement corresponds to insertion of the needle 2 into the injection site, e.g. subcutaneous body tissue and removal from the injection site, respectively.

A drive mechanism 9 for the needle 2 is arranged as a bi-stable mechanism with a first link 10 and a telescopable second link 11 loaded by a spring 12. The first link 10 is connected to an anchor point in a case (not illustrated) by a first pivot joint 5 which may be arranged in the middle of the first link 10. One end of the first link 10 is adapted to abut an upper prong 7.1 or a lower prong 7.2 on the forked needle retainer 7 by a cam 13 on the first link 10. The second link 11 comprises a first part 11.1 and a second part 11.2 telescoped with each other. One end of the second link is connected to another anchor point in the case (not illustrated) by a second pivot joint 14 such that the first and second pivot joint 5, 14 cannot move relative each other. The other ends of both the first link 10 and the second link 11 are interconnected by a third pivot joint 15 such that pivoting movement of one of the links 10, 11 causes pivoting movement of the other link 11, 10 thereby also changing the length of the telescopable second link 11. The length of the second link 11 is shortest if the third pivot joint 15 is situated on an imaginary connecting line between the cam 13 and the second pivot joint 14 in a central position. As the third pivot joint 15 is moved above or below the connecting line between the cam 13 and the second pivot joint 14 the length of the second link 11 increases. The first part 11.1 and second part 11.2 of the second link 11 are biased apart by the spring 12 such that the spring 12 is compressed by shortening the second link 11. The force of the spring 12 is therefore highest in the central position of the third pivot joint 15.

The spring force thus forces the third pivot joint 15 out of the central position towards one of two end positions which may be defined by a stop (not illustrated) limiting the maximum length of the second link 11. In these end positions the drive mechanism 9 is stable due to the remaining force of the spring 12 while the central position is transitional.

Instead of the button 17 and button link 18 of the first embodiment a motor-driven wheel 21 is arranged for rotating the first link 10. In an exemplary embodiment a gear may be arranged between the motor and the wheel 21. The wheel 21 comprises a first protrusion 21.1 and a second protrusion 21.2 for engaging the first link 10. The first protrusion 21.1 is adapted to rotate the first link 10 in a first rotational direction S1 for switching the drive mechanism 9 from the stable lower end position LEP to the stable upper end position UEP. The second protrusion 21.2 is adapted to rotate the first link 10 in an opposite second rotational direction S2 for switching the drive mechanism 9 from the stable upper end position UEP to the stable lower end position LEP. The first protrusion 21.1 and the second protrusion 21.2 are angularly spaced from each other, e.g. by 90 degrees, allowing for some free rotation of the first link 10. Although the first link 10 in FIGS. 8 and 9 exhibits the guide track 19 of the first embodiment this guide track 19 is not needed in the embodiment of FIGS. 8 and 9.

Figure 10:
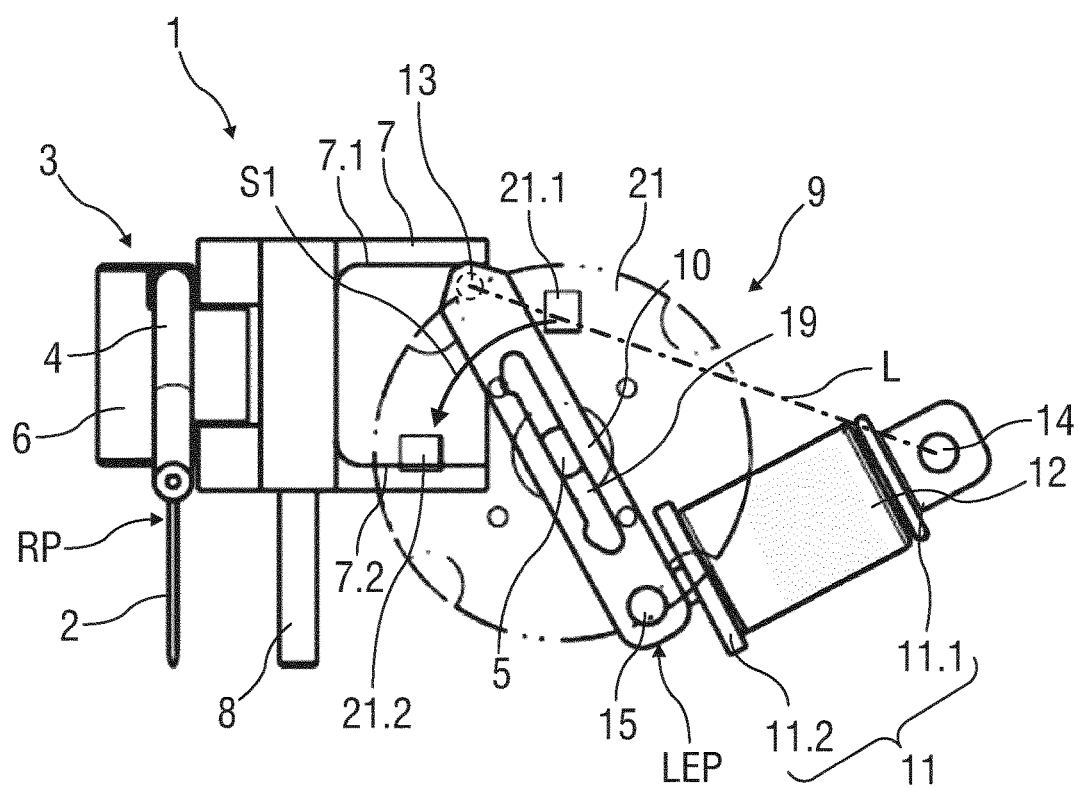
FIG. 10 is a schematic side view of the second embodiment of the insertion arrangement in an initial position with a bistable drive mechanism in a stable lower end position and the needle in a retracted position.

A sequence of operation of the insertion arrangement 1 is as follows:

FIG. 10 is a schematic side view of the insertion arrangement 1 in an initial position. The disposable unit 3 with the needle base 6, the needle 2 and the tube 4 has been inserted in the forked needle retainer 7. The third pivot joint 15 is held in a stable lower end position LEP below an imaginary connecting line L between the cam 13 and the second pivot joint 14 by the spring 12. The cam 13 thus engages the upper prong 7.1 on the forked needle retainer 7 keeping it in a retracted position RP.

Figure 11:
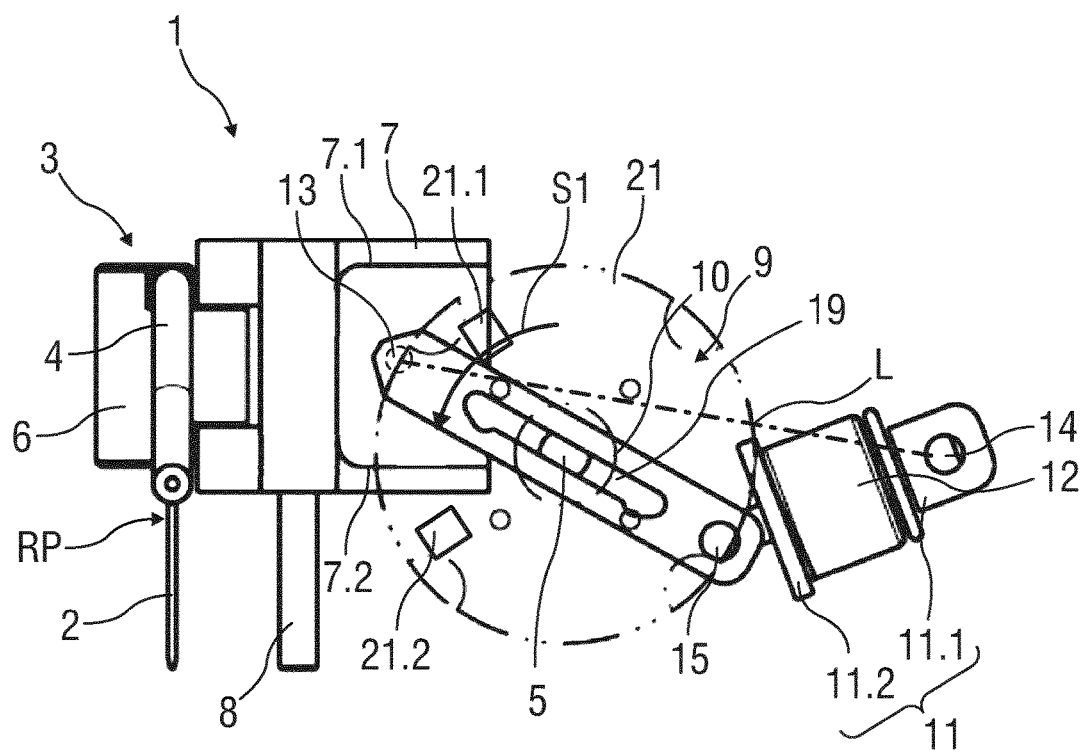
FIG. 11 is a schematic side view of the second embodiment of the insertion arrangement during rotation of a wheel thus entraining a first link of the drive mechanism in a first rotational direction.

FIG. 11 is a schematic side view of the insertion arrangement 1 during rotation of the wheel 21 thus entraining the first link 10 in the first rotational direction S1 by the first protrusion 21.1. Due to the rotation of the first link 10 the cam 13 is removed from the upper prong 7.1 on the forked needle retainer 7 towards the lower prong 7.2. The first link 10 is rotated about the first pivot joint 5 thereby telescoping the first part 11.1 and second part 11.2 and further compressing the spring 12. Due to the distance between the upper prong 7.1 and the lower prong 7.2 the cam 13 is disengaged from the forked needle retainer 7 such that the forked needle retainer 7, the needle base 6 and the needle 2 remain in the retracted position RP. A spring or detent (not illustrated) may be arranged for securing the forked needle retainer 7 in the retracted position RP.

Figure 12:
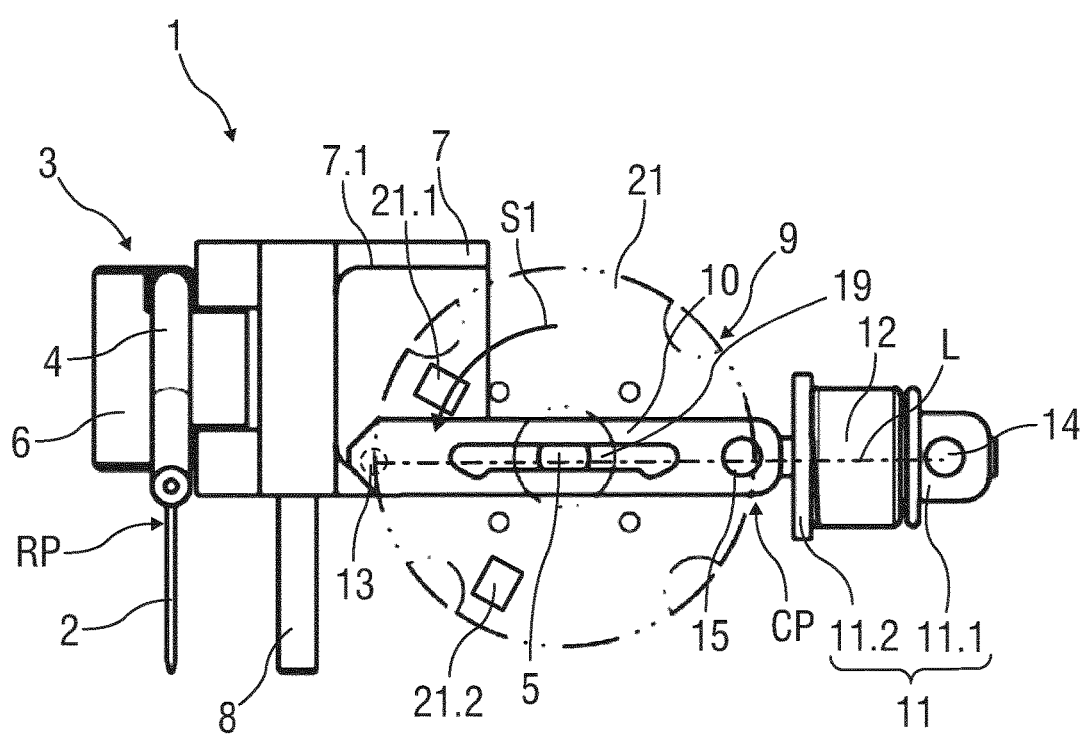
FIG. 12 is a schematic side view of the second embodiment of the insertion arrangement with the drive mechanism in a transitional central position.

FIG. 12 is a schematic side view of the insertion arrangement 1 with the third pivot joint 15 in the central position CP. Due to further rotation of the wheel 21 the first link 10, second link 11 and third pivot joint 15 are aligned on the imaginary connecting line L. The spring 12 is therefore fully compressed and the first part 11.1 and second part 11.2 fully telescoped. The cam 13 on the first link 10 is contacting the lower prong 7.2 but not yet exerting any force to it. The forked needle retainer 7, the needle base 6 and the needle 2 therefore remain in the retracted position RP.

Figure 13:
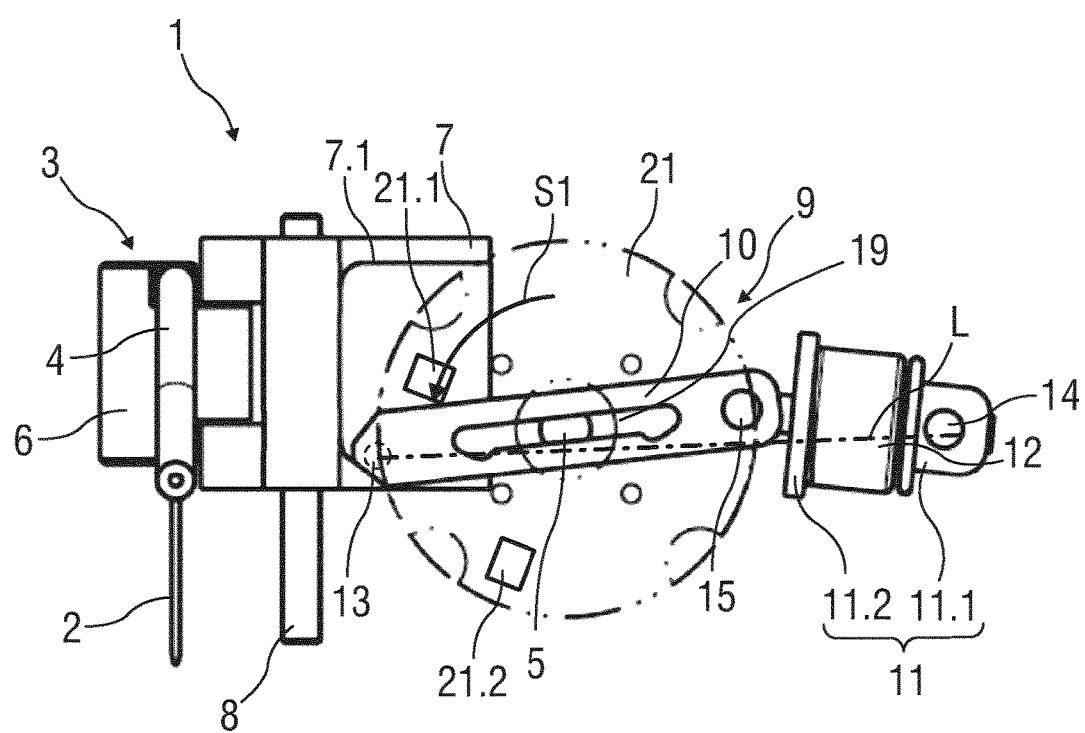
FIG. 13 is a schematic side view of the second embodiment of the insertion arrangement with the wheel rotated further for moving the drive mechanism out of the transitional position.

FIG. 13 is a schematic side view of the insertion arrangement 1 with the wheel 21 rotated further in the first rotational direction S1. Therefore the third pivot joint 15 is moved out of its central position CP below the imaginary connecting line L. This allows the spring 12 to suddenly relax, telescoping the first part 11.1 and second part 11.2 apart and rotating the first link 10 further such that the cam 13 pushes on the lower prong 7.2 of the forked needle retainer 7 thereby moving the forked needle retainer 7, the needle base 6 and the needle 2 into an extended position EP in order to rapidly inserting the needle 2 into an injection site. The first link 10 can freely rotate until abutting the second protrusion 21.2 such that the speed of the movement of the forked needle retainer 7 is determined by the spring 12 and not affected by the wheel 21.

Figure 14:
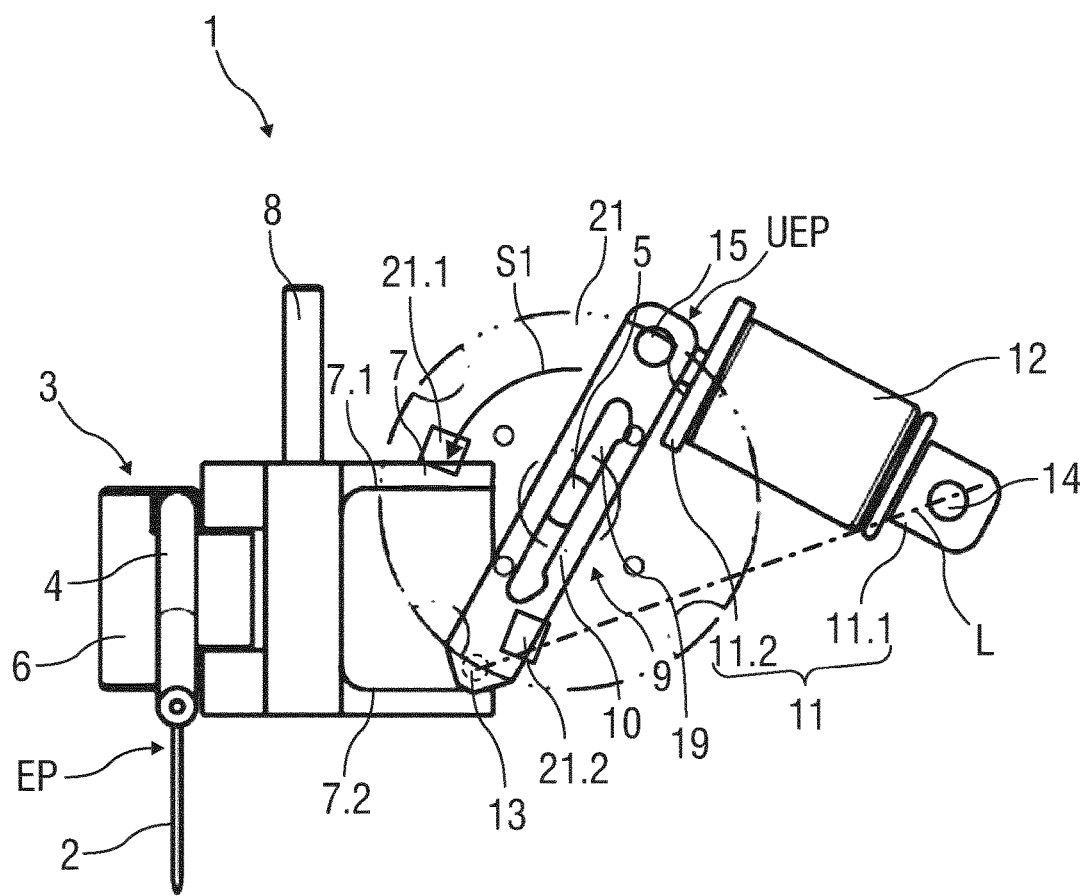
FIG. 14 is a schematic side view of the insertion arrangement with the drive mechanism in a stable upper end position.

FIG. 14 is a schematic side view of the insertion arrangement 1 with the drive mechanism 9 having reached its stable upper end position UEP due to the force of the spring 12. The forked needle retainer 7, needle base 6 and needle 2 have been moved to the extended position EP. The needle 2 has therefore reached its maximum insertion depth. As the second protrusion 21.2 is in contact with the first link 10 rotation of the wheel 21 in the second rotational direction S2 would cause the drive mechanism 9 to switch back to the stable lower end position LEP such that the cam 13 would contact the upper prong 7.1 and retract the forked needle retainer 7, the needle base 6 and the needle 2 into the retracted position RP as in FIG. 10. This switching is achieved in an analogous manner as from the stable lower end position LEP to the stable upper end position UEP. The speed, e.g. slow, middle, fast, of the movement of the forked needle retainer 7 between the retracted position RP and the extended position EP and vice versa can be influenced by selecting a spring 12 with an appropriate force and/or by programming the motor operation appropriately.

The drive mechanism 9 could be modified to comprise only one pivoted link, wherein the spring 12 would be connected with one end to the link and the other end to a fixed anchor point distinct from the anchor point to which the link is connected. The spring 12 may be arranged as a compression spring or as a tension spring.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp- Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

LIST OF REFERENCES 1 insertion arrangement
2 needle
3 disposable unit
4 tube
5 first pivot joint
6 needle base
7 needle retainer
7.1 upper prong
7.2 lower prong
8 linear guide
9 drive mechanism
10 first link
11 second link
11.1 first part
11.2 second part
12 spring
13 cam
14 second pivot joint
15 third pivot joint
16 fourth pivot joint
17 button
18 button link
19 guide track
19.1 long slot
19.2 first bulge
19.3 second bulge
20 button cam
21 wheel
21.1 first protrusion
21.2 second protrusion
DBP depressed button position
EBP extended button position
EP extended position
L imaginary connecting line
LEP lower end position
UEP upper end position
RP retracted position
S1 first rotational direction
S2 second rotational direction

The invention claimed is:

1. A drive mechanism for a needle insertion arrangement, the drive mechanism comprising:
  a bistable mechanism with at least one pivoted link having two stable end positions (LEP, UEP) and an instable transitional central position (CP);
  a spring biasing the at least one pivoted link out of the instable transitional central position (CP), wherein at least one trigger unit is arranged for moving the at least one pivoted link out of at least one of the stable end positions (LEP, UEP) towards and beyond the instable transitional central position (CP) against the bias of the spring; and
  a forked needle retainer adapted to retain an injection needle, the forked needle retainer arranged to be linearly moved between a retracted position (RP) and an extended position (EP), wherein one end of the at least one pivoted link is adapted to abut an upper prong and a lower prong on the forked needle retainer, wherein the upper prong is spaced from the lower prong for allowing a pre-determined free travel of the at least one pivoted link between disengaging one of the prongs and engaging the other one of the prongs.

2. The drive mechanism according to claim 1, wherein the at least one pivoted link comprises a cam for engaging the upper prong and the lower prong.

3. The drive mechanism according to claim 1, wherein the at least one pivoted link comprises a pivoted first link and a pivoted second link interconnected by a pivot joint such that pivoting movement of the pivoted first link or the pivoted second link causes pivoting movement of the pivoted second link or the pivoted first link.

4. The drive mechanism according to claim 3, wherein the pivot joint is a third pivot joint, wherein the pivoted first link is connected to an anchor point by a first pivot joint, wherein one end of the pivoted second link is connected to another anchor point by a second pivot joint having a fixed position relative the first pivot joint.

5. The drive mechanism according to claim 3, wherein the pivoted second link comprises a first part and a second part telescoped with each other such that a length of the pivoted second link is changed when the second link is being pivoted.

6. The drive mechanism according to claim 5, wherein the first part and the second part of the second link are biased apart by the spring.

7. The drive mechanism according to claim 3, wherein the at least one trigger unit is arranged as a button connected to one of the pivoted first link or the pivoted second link.

8. The drive mechanism according to claim 7, comprising a button link pivoted about a fourth pivot joint in the button with one end and comprising a button cam for engaging a guide track in the pivoted first link, wherein the first pivot joint is arranged between two ends of the guide track.

9. The drive mechanism according to claim 8, wherein the guide track comprises a long slot allowing movement of the button cam from one end of the guide track to the other after the pivoted first link has been moved to one of the stable end positions (LEP, UEP) and after release of the button such that another operation of the button switches the pivoted first link into the respective other one of the stable end positions (UEP, LEP).

10. The drive mechanism according to claim 9, wherein the guide track comprises a first bulge at one end of the guide track and a second bulge at another end of the guide track.

11. The drive mechanism according to claim 3, wherein the trigger unit comprises a motor-driven wheel comprising a first protrusion adapted to engage the pivoted first link when the motor-driven wheel is rotated in a first rotational direction (S1) and comprising a second protrusion adapted to engage the pivoted first link when the wheel is rotated in an opposite second rotational direction (S2).

12. The drive mechanism according to claim 11, wherein the first protrusion and the second protrusion are angularly spaced from each other allowing for a pre-determined free rotation of the pivoted first link relative the wheel.

13. An insertion-arrangement for moving an injection needle between a retracted position (RP) and an extended position (EP), the insertion arrangement comprising:
a disposable unit comprising a needle base to which the injection needle is fixed; and
a drive mechanism comprising:
a bistable mechanism with at least one pivoted link having two stable end positions (LEP, UEP) and an instable transitional central position (CP);
a spring biasing the at least one pivoted link out of the instable transitional central position (CP), wherein at least one trigger unit is arranged for moving the at least one pivoted link out of at least one of the stable end positions (LEP, UEP) towards and beyond the instable transitional central position (CP) against the bias of the spring; and
a forked needle retainer adapted to retain an injection needle, the forked needle retainer arranged to be linearly moved between a retracted position (RP) and an extended position (EP), wherein one end of the at least one pivoted link is adapted to abut an upper prong and a lower prong on the forked needle retainer,
wherein the upper prong is spaced from the lower prong for allowing a pre-determined free travel of the at least one pivoted link between disengaging one of the prongs and engaging the other one of the prongs,
wherein the forked needle retainer is adapted to retain the needle base.

14. The insertion arrangement according to claim 13, wherein the at least one pivoted link comprises a cam for engaging the upper prong and the lower prong.

15. The insertion arrangement according to claim 13, wherein the at least one pivoted link comprises a pivoted first link and a pivoted second link interconnected by a pivot joint such that pivoting movement of the pivoted first link or the pivoted second link causes pivoting movement of the pivoted second link or the pivoted first link.

16. The insertion arrangement according to claim 15, wherein the pivot joint is a third pivot joint, wherein the pivoted first link is connected to an anchor point by a first pivot joint, wherein one end of the pivoted second link is connected to another anchor point by a second pivot joint having a fixed position relative the first pivot joint.

17. The insertion arrangement according to claim 15, wherein the pivoted second link comprises a first part and a second part telescoped with each other such that a length of the pivoted second link is changed when the second link is being pivoted.

18. An auto-injector comprising:
an insertion arrangement for moving an injection needle between a retracted position (RP) and an extended position (EP), the insertion arrangement comprising:
a disposable unit comprising a needle base to which the injection needle is fixed; and
a drive mechanism comprising:
a bistable mechanism with at least one pivoted link having two stable end positions (LEP, UEP) and an instable transitional central position (CP);
a spring biasing the at least one pivoted link out of the instable transitional central position (CP), wherein at least one trigger unit is arranged for moving the at least one pivoted link out of at least one of the stable end positions (LEP, UEP) towards and beyond the instable transitional central position (CP) against the bias of the spring;
a forked needle retainer adapted to retain an injection needle, the forked needle retainer arranged to be linearly moved between a retracted position (RP) and an extended position (EP), wherein one end of the at least one pivoted link is adapted to abut an upper prong and a lower prong on the forked needle retainer, wherein the forked needle retainer is adapted to retain the needle base, wherein the upper prong is spaced from the lower prong for allowing a pre-determined free travel of the at least one pivoted link between disengaging one of the prongs and engaging the other one of the prongs; and a drug container coupled to the injection needle, wherein the drug container contains at least one pharmaceutically active compound.

\* \* \* \* \*